United States Patent [19]

Nicholson et al.

[11] 4,209,638

[45] Jun. 24, 1980

[54] PREPARATION OF THERAPEUTIC AGENTS

[75] Inventors: John S. Nicholson, Chilwell; James G. Tantum, Nuthall, both of England

[73] Assignee: The Boots Company Limited, Nottingham, England

[21] Appl. No.: 945,481

[22] Filed: Sep. 25, 1978

Related U.S. Application Data

[63] Continuation-in-part of Ser. No. 884,422, Mar. 8, 1978, abandoned.

[30] Foreign Application Priority Data

Mar. 8, 1977 [GB] United Kingdom ................. 9697/77
Jan. 18, 1978 [GB] United Kingdom ................. 1946/78

[51] Int. Cl.$^2$ ...................... C07B 19/00; C07B 20/00
[52] U.S. Cl. .................................. 562/401; 260/315; 260/326.1; 260/326.2; 260/326.47; 260/335; 260/346.22; 260/347.3; 260/465 D; 544/35; 546/89; 549/72; 549/79; 562/402; 548/180; 548/217
[58] Field of Search .............................. 562/401, 402; 260/332.3 R, 347.3, 326.47, 332.2 A, 326.1, 307 D, 315, 304 R, 346.22, 335, 326.2, 465 D; 546/89; 544/35

[56] References Cited

U.S. PATENT DOCUMENTS

| | | | |
|---|---|---|---|
| 3,600,437 | 8/1971 | Marshall | 562/401 |
| 3,683,015 | 8/1972 | Dyson | 562/401 |
| 3,686,183 | 8/1972 | Dyson | 562/401 |
| 3,957,861 | 5/1976 | Herr et al. | 562/401 |

OTHER PUBLICATIONS

Eliel, *Stereochemistry of Carbon Compounds*, pp. 46–53, (1962).

*Primary Examiner*—Jane S. Myers
*Attorney, Agent, or Firm*—Gordon W. Hueschen

[57] ABSTRACT

Disclosed is a process for increasing the proportion of a desired enantiomer of a 2-arylpropionic acid which comprises heating at a temperature of at least 80° C. a mixture comprising an inert liquid organic diluent and a salt of the 2-arylpropionic acid with an enantiomer of a chiral organic nitrogenous base, the base and the diluent being such that the salt of the racemic acid has a solubility of 0.1 to 10% $w/v$ in the diluent at the operating temperature and in which process a proportion of the salt is undissolved in the diluent, whereby a proportion of one optical isomer of the acid component of the salt is converted into its enantiomer, and collecting the salt of which the acid component has an increased proportion of that enantiomer.

22 Claims, No Drawings

PREPARATION OF THERAPEUTIC AGENTS

This application is a continuation-in-part of our prior-filed co-pending application Ser. No. 884,422, filed Mar. 8, 1978, now abandoned.

This invention relates to the preparation of optically active 2-arylpropionic acids. Certain 2-arylpropionic acids are known to have valuable biological properties and in particular anti-inflammatory properties.

It is believed that, with some 2-arylpropionic acids, biological activity of one of the optical isomers is greater than that of its enantiomer and it is desirable that a simple method of obtaining a preponderance of one enantiomer be achieved.

Conventional resolution techniques involving separation of a mixture of diastereoisomeric salts of an acid are usually very tedious since they often require several recrystallisation stages and also racemisation of the unwanted enantiomer to improve yields.

We have now found that a desired enantiomer of a 2-arylpropionic acid can be obtained from a mixture of diastereoisomeric salts in a simple manner in which generally fewer stages are involved than in conventional resolution techniques.

According to the invention there is provided a process for increasing the proportion of a desired enantiomer of a 2-arylpropionic acid which comprises heating at a temperature of at least 80° C. a mixture comprising an inert liquid organic diluent and a salt of the 2-arylpropionic acid with an enantiomer of a chiral organic nitrogenous base, the base and the diluent being such that the salt of the racemic acid has a solubility of 0.1 to 10% w/v in the diluent at the operating temperature and in which process a proportion of the salt is undissolved in the diluent, whereby a proportion of one optical isomer of the acid component of the salt is converted into its enantiomer, and collecting the salt of which the acid component has an increased and preponderant proportion of that enantiomer.

The 2-arylpropionic acid is generally one in which the aryl group is of formula

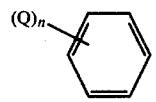

in which n is an integer of 1 to 4, preferably 1 or 2, and Q is the same or different and is selected from $C_{1-4}$ alkyl, e.g. methyl; aralkyl, e.g. benzyl; cycloalkyl, e.g. of three to seven carbon atoms, and especially cyclohexyl; alkyl substituted cycloalkyl, e.g. monomethyl and monoethyl substituted cyclohexyl; aryl, e.g. phenyl and phenyl substituted with, for example 1 or 2 alkyl, preferably $C_{1-4}$ alkyl, alkoxy, preferably $C_{1-4}$ alkoxy, alkylthio preferably $C_{1-4}$ alkylthio, cyano or halogen; alkoxy, preferably $C_{1-4}$ alkoxy; cycloalkoxy, e.g. cyclohexyloxy; aryloxy, e.g. phenoxy and phenoxy substituted with, for example 1 or 2 halogen atoms especially chlorine or fluorine; alkylthio, preferably $C_{1-4}$ alkylthio; aralkylthio; cycloalkylthio; arylthio, e.g. phenylthio; arylcarbonyl, e.g. benzoyl and thenoyl; cycloalkenyl e.g. cyclohexenyl; trifluoromethyl; halogen, e.g. fluorine or chlorine; furyl; pyrrolidinyl; pyrrolyl; pyrrolinyl; thienyl; or 1-oxo-2-isoindolinyl; or two Q groups together form a carbocyclic or heterocyclic ring, which rings may be aromatic and may be substituted. Examples of groups formed by two Q groups together with the benzene to which they are attached include naphthyl and substituted naphthyl, especially alkoxynaphthyl, fluorenyl, benzoxazolyl, optionally substituted e.g. by p-chlorophenyl, carbazolyl, optionally substituted by chloro, benzothiazolyl, optionally substituted by phenyl, phenothiazinyl, optionally substituted by alkoxy and alkyl, benzofuranyl optionally substituted by phenyl, benzopyrano [2,3-b]-pyridinyl, and 9-oxoxanthenyl.

Instead of being a substituted phenyl the aryl group may be a heteroaryl group e.g. benzothiazolyl, pyrrolyl, or thienyl, which groups may be substituted by groups designated for Q above.

Particularly preferred compounds are those in which the aryl group is of the formula:

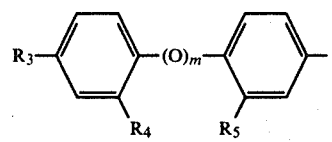

in which m is 0 or 1, and $R_3$, $R_4$ and $R_5$ may be the same or different and are selected from hydrogen, chlorine, fluorine, hydroxy and methoxy. Especially preferred are those compounds in which m is 0.

Other preferred aryl groups include 2-(6-methoxy-2-naphthyl) and those in which n is 1 and Q is in the 3-position and is benzoyl or phenoxy or is in the 4-position and is 1-oxo-2-isoindolinyl.

The invention is particularly applicable to 2-(2-fluoro-4-biphenyl)propionic acid and especially in obtaining a preponderance of the (+)-isomer.

The invention can be carried out by using a racemic 2-arylpropionic acid, either enantiomer of a 2-arylpropionic acid, or mixtures containing a preponderance of either enantiomer. Depending on the particular salts involved the process may result in an increase of either enantiomer of the acid. The use of racemic acid results in formation of a salt containing a preponderance of one enantiomer of the acid. The process does not convert material to give salt of one enantiomer of the acid exclusively in all cases so it is often desirable to treat the material obtained to a minimal number, generally not more than two, conventional recrystallisation stages or other means of purification.

The desired acid may be recovered from the salt by conventional means, e.g. by acidification of the salt with a dilute mineral acid followed by extraction from the aqueous mixture with a suitable organic solvent. Recrystallisation of the acid may increase the optical purity still further.

It will be appreciated that the choice of base will depend on the 2-arylpropionic acid. The choice of diluent will depend on the 2-arylpropionic acid and the base.

Generally the base is an α-monosubstituted alkylamine, and preferably an α-monosubstituted ethylamine, especially an α-phenylethylamine in which the phenyl ring may be substituted by one or more groups such as alkyl e.g. $C_{1-4}$ alkyl, especially isopropyl, halogen, e.g. chlorine or fluorine, alkoxy e.g. $C_{1-4}$ alkoxy, especially methoxy. Particularly preferred bases are (−)-α-methylbenzylamine and (−)-α-(2-methoxyphenyl)ethylamine. Other suitable bases include (−)-α-(4-isopropylphenyl)ethylamine, (−)-α-(3-chlorophenyl)ethylamine, (−)-α-(4-fluorophenyl)ethylamine (−)-α-(3-fluorophenyl)ethylamine, (−)-α-(2-fluorophenyl) ethylamine, (−)-α-(2-chlorophenyl)ethylamine, (+)-α-(2-methoxyphenyl)ethylamine, (−)-α-(2,6-dimethoxyphenyl) ethylamine and also (+)-α-cyclohexylethylamine.

Preferably the mixture of diluent and salt is heated at a temperature of 90°–150° C. e.g. 95°–130° C. The heating is usually carried out for at least 1 hour e.g. 8–96 hours.

It is preferred that the ratio of the salt to the diluent is from 1:1 to 1:100 w/v, e.g. 1:5 to 1:15 w/v.

Preferably the solubility of the salt of the racemic acid in the diluent at the operating temperature is from 0.5 to 2% w/v.

Preferably 50 to 98% by weight of the salt e.g. 80–95%, is undissolved in the diluent at the operating temperature.

The inert diluent is a liquid at the temperature at which the mixture is heated and may comprise one or more organic compounds. Usually the diluent is of low polarity and for example may comprise one or more hydrocarbons. The diluent is preferably a mixture of hydrocarbons which are predominantly aliphatic and it preferably has a boiling point in the range 110°–135° C. Polar compounds, in amounts of e.g. up to 1% may be included in the diluent.

It is preferable that the diluent is such that the reaction can be carried out under reflux conditions.

It may be desirable, to avoid by-product formation, that heating is carried out under an inert atmosphere, e.g. nitrogen.

The invention is illustrated in the following Examples in which flurbiprofen is (±)-2-(2-fluoro-4-biphenylyl)-propionic acid. Unless otherwise stated specific rotations were measured in ethanol at a concentration of 1% w/v and at ambient temperature.

EXAMPLES 1 TO 38

Various mixtures comprising an amine salt of a 2-arylpropionic acid and a diluent consisting of one or more liquid organic compounds were stirred and heated. On completion of the heating, the hot mixture were filtered through a steam heated Buchner funnel, the salts were washed with the hot diluent, dried in vacuo, acidified with dilute sulphuric or hydrochloric acid and the acid mixtures extracted with ether. The ether extracts were washed with water, dried and evaporated to give 2-arylpropionic acids having a different optical activity from the acid component of the salt from the start of the experiment.

The details and results of various Examples are given in Table I.

TABLE I

| Ex. No. | Acid | Amine | Diluent | Diluent per g. of salt (ml) | Solubility of salt of (±) acid in diluent at reaction temperature (ml/g) | Reaction Temperature (°C.) | Reaction Time (hours) | Yield of salt (%) | $[\alpha]_D$ of acid (°) recovered |
|---|---|---|---|---|---|---|---|---|---|
| 1 | A2 | G | R | 10 | 110 | 115 | 24 | 58.0 | +23.6 |
| 2 | A2 | G | R | 10 | 110 | 115 | 72 | 71.0 | +35.3 |
| 3 | A1 | G | R | 10 | 110 | 115 | 72 | 80.0 | +31.3 |
| 4 | A1 | H | R | 10 | 85 | 115 | 72 | 61.2 | +34.2 |
| 5 | A1 | J | R | 10 | 100 | 115 | 72 | 61.3 | +29.3 |
| 6 | B | G | R | 10 | 100 | 115 | 72 | 71.0 | +34.9 |
| 7 | C | G | R | 10 | 90 | 115 | 72 | 69.0 | +27.9 |
| 8 | A1 | G | S | 10 | 26 | 117 | 72 | 73.3 | +33.4 |
| 9 | A1 | G | T | 10 | 15.5 | 117 | 72 | 74.5 | +33.0 |
| 10 | A1 | G | U1 | 10 | 68.4 | 113 | 72 | 75.3 | +33.4 |
| 11 | A1 | G | R | 10 | 186 | 108 | 72 | 76.5 | +25.5 |
| 12 | A1 | G | R | 10 | 352 | 97 | 72 | 77.0 | +15.8 |
| 13 | A3 | G | V | 10 | 72 | 115 | 72 | 66.5 | +27.6 |
| 14 | A1 | K | R | 10 | 33 | 115 | 72 | 49.0 | +37.0 |
| 15 | A1 | G | W | 10 | 124 | 125 | 8 | 71.0 | +22.5 |
| 16 | A1 | G | W | 10 | 124 | 125 | 96 | 73.5 | +33.6 |
| 17 | A1 | G | X | 10 | 57 | 126 | 72 | 70.0 | +35.4 |
| 18 | A1 | G | Y | 10 | 114 | 115 | 72 | 76.0 | +32.4 |
| 19 | A1 | L1 | R | 14.4 | 160 | 115 | 72 | 84.3 | −41.45 |
| 20 | A1 | M | R | 9.4 | 94 | 115 | 72 | 64.0 | +37.3 |
| 21 | A4 | G | R | 10 | 110 | 115 | 72 | 80.5 | +35.0 |
| 22 | A1 | G | U2 | 10 | 57 | 112 | 72 | 66.0 | +32.4 |
| 23 | D | G | R | 6.7 | 58 | 115 | 72 | 67.7 | +27.3 |
| 24 | A1 | G | T | 3 | 15.5 | 117 | 72 | 87.0 | +33.3 |
| 25 | A1 | G | S | 5 | 26 | 117 | 72 | 79.0 | +35.4 |
| 26 | A1 | N | R | 6 | 66 | 115 | 72 | 69.5 | −35.2 |
| 27 | A1 | L2 | R | 15.2 | 160 | 115 | 72 | 80.1 | +42.1 |
| 28 | A1 | O | R | 4 | 40 | 115 | 72 | 57.6 | +37.66 |
| 29 | A1 | P | R | 6 | 59 | 115 | 72 | 58.0 | +34.9 |
| 30 | E | G | R | 3 | 28 | 115 | 72 | 65.4 | +12.6 |
| 31 | F | G | Z | 7 | 90 | 115 | 72 | 57.7 | +32.3 |
| 32 | A1 | Q1 | R | 2.6 | 52 | 95 | 72 | 90.2 | −7.4 |
| 33 | F1 | G | R | 1.4 | 15 | 115 | 48 | 80.6 | +25.8 |
| 34 | A1 | Q2 | R | 1.4 | 14 | 115 | 72 | 53.6 | −30.9 |
| 35 | A5 | Q3 | R | 5.0 | ND | 95 | 72 | 86.6 | +37.9 |
| 36 | A1 | Q4 | R | 1.9 | ND | 95 | 72 | 55.5 | +41.6 |
| 37 | A1 | Q5 | R | 2.5 | 28 | 115 | 72 | 62.5 | +23.2 |
| 38 | A1 | G | Z1 | 5.0 | 46 | 117 | 72 | 83.3 | +34.9 |

KEY TO TABLE I p-arylpropionic acids

ND = Not determined

TABLE I-continued

| Ex. No. | Acid | Amine | Diluent | Diluent per g. of salt (ml) | Solubility of salt of (±) acid in diluent at reaction temperature (ml/g) | Reaction Temperature (°C.) | Reaction Time (hours) | Yield of salt (%) | $[\alpha]_D$ of acid (°) recovered |
|---|---|---|---|---|---|---|---|---|---|

A1 = (±)-2(2-fluoro-4-biphenylyl)propionic acid
A2 = 2-(2-fluoro-4-biphenylyl)propionic acid, having $[\alpha]_D$ −30°
A3 = 2-(2-fluoro-4-biphenylyl)propionic acid, having $[\alpha]_D$ −44.7°   Optically pure isomers
A4 = 2-(2-fluoro-4-biphenylyl)propionic acid, having $[\alpha]_D$ +8.9°   have $[\alpha]_D$ of + or −44.7°
A5 = 2-(2-fluoro-4-biphenylyl)propionic acid, having $[\alpha]_D$ +19.7°
B = (±)-2-(2'-fluoro-4-biphenylyl)propionic: Optically pure (+)-isomer has $[\alpha]_D$ +50.3°
C = (±)-2-(2,2'-2-(2,2',4'-trifluoro-4-biphenylyl)propionic acid: Optically pure (+)-isomer has $[\alpha]_D$ + 35.9°
D = (±)-2-(6-methoxy-2-naphthyl)propionic acid: Optically pure (+)-isomer has $[\alpha]_D$ + 66°
E = (±)-2-[-2-[4-(2-fluorophenoxy)phenyl]propionic acid: Optically pure (+)-isomer has $[\alpha]_D$ + 42.0°
F = (±)-2-(2-hydroxy-4-biphenylyl)propionic acid: Optically pure (+)-isomer has $[\alpha]$ + 47.6°
F1 = (±)-2-(4-isobutylphenyl)propionic acid: Optically pure (+)-isomer has $[\alpha]_D$ = + 57.7°
*Specific rotations of this acid were measured in chloroform at a concentration of 1% w/v.

Amines

G = (−)-α-methylbenzylamine
H = (−)-α-(4-isopropylphenyl)ethylamine
J = (+)-α-cyclohexylethylamine
K = (−)-α-(3-chlorophenyl)ethylamine
L1 = (+)-α-(2-methoxyphenyl)ethylamine
L2 = (−)-α-(2-methoxyphenyl)ethylamine
M = (−)-α-(4-fluorophenyl)ethylamine
N = (+)-α-(2-fluorophenyl)ethylamine
O = (−)-α-(2-chlorophenyl)ethylamine Q1 = (−)-α-(2,5-dimethoxyphenyl)ethylamine
Q2 = (−)-α-(2-methylphenyl)ethylamine
Q3 = (+)-α-(2,6-dimethoxyphenyl)ethylamine
Q4 = (−)-α-(2-ethoxyphenyl-1)ethylamine
Q5 = (+)-α-(2-methylthiophenyl)ethylamine

Solvents

R = Petroleum fraction, initial b.p. 112° C.
S = (−)-α-pinene
T = myrcene
U1 = 85% R + 15% toluene
U2 = 67% R + 33% toluene
V = Petroleum fraction, b.p. range 120° C.–160° C.
W = Petroleum fraction, initial b.p. 125° C.
X = Octane
Y = Petroleum fraction, initial b.p. 115° C., containing 1% n-butanol
Z = Toluene
Z1 = 1-decene

EXAMPLE 39

Flurbiprofen (4.75 kg.) was mixed with a petroleum fraction b.p. 125° C. (48 liters) and the mixture stirred under nitrogen and heated to form a solution. (−)-α-Methylbenzylamine (2.35 kg.) in the same petrol (23 liters) was added with stirring and the mixture then heated under reflux under nitrogen for 72 hours. The internal temperature was 125° C. The mixture was then filtered, and the salt was washed with the hot petrol and dried to give the (−)-α-methylbenzylamine salt of 2-(2-fluoro-4-biphenylyl)propionic acid (5.4 k.g.) in 76% yield. A small portion of this was acidified to give 2-(2-fluoro-4-biphenylyl)propionic acid having $[\alpha]_D$+33°. The remainder was recrystallised from isopropanol and a portion acidified to give 2-(2-fluoro-4-biphenylyl)propionic acid having $[\alpha]_D$+41°.

The remainder of the recrystallised salt (4.3 kg.) was mixed with light petroleum (b.p. 102°–120° C.; 35 liters) and water (37 liters), and the mixture stirred under nitrogen. Concentrated hydrochloric acid (1 kg.) was added and the mixture refluxed for 1 hour. The hot organic layer was separated, washed with water, filtered, cooled and the product collected by filtration, washed with hexane and dried to give 2-(2-fluoro-4-biphenylyl)propionic acid, having $[\alpha]_D$+43.7° representing 98% optical purity.

The filtrate after the initial 72 hour heating of the salt together with solid recovered from mother liquors from the isopropanol recrystallisation of salt and the petrol crystallisation of the acid were all recycled for treatment with a further quantity of flurbiprofen.

The amine salt of the racemic acid has a solubility in the petroleum fraction of 124 ml/g. at 125° C.

EXAMPLE 40

The (−)-α-methylbenzylammonium salt (1 part by weight) of flurbiprofen was mixed with light petroleum (b.p. 40°–60° C.; 10 parts by volume) and heated at 116° C. in a sealed autoclave for 72 hours. The mixture was then cooled and filtered and the salt was washed with light petroleum and dried in vacuo to give a 93.5% yield of salt which gave 2-(2-fluoro-4-biphenylyl)propionic acid having $[\alpha]_D$+21.9°.

What we claim is:

1. A process for increasing the proportion of a desired enantiomer of a 2-arylpropionic acid which comprises heating at a temperature of at least 80° C. a mixture comprising a salt of said 2-arylpropionic acid with an enantiomer of a chiral organic nitrogenous base and an inert liquid organic diluent in which the salt of the racemic acid has a solubility of 0.1 to 10% w/v at the operating temperature, and is used in an amount such that a portion of the salt is undissolved in the diluent, continuing the heating until a portion of one optical isomer of the acid component of the salt is converted into its enantiomer, then recovering the solid salt in which the acid compound now has an increased and preponderant proportion of that enantiomer, and separating the acid component therefrom.

2. A process according to claim 1 in which the 2-arylpropionic acid is one in which the aryl group is of the formula:

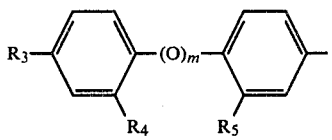

in which m is 0 or 1, and R₃, R₄ and R₅ may be the same or different and are selected from hydrogen, chlorine, fluorine, hydroxy and methoxy.

3. A process according to claim 2 in which the 2-arylpropionic acid is selected from 2-(2-fluoro-4-biphenylyl) propionic acid, 2-(2'-fluoro-4-biphenylyl)propionic acid, 2-(2,2',4'-trifluoro-4-biphenylyl)propionic acid, 2-(2-hydroxy-4-biphenylyl)propionic acid and 2-[4-(2-fluorophenoxy)phenyl]propionic acid.

4. A process according to claim 1 in which the 2-arylpropionic acid is 2-(6-methoxy-2-naphthyl)propionic acid.

5. A process according to claim 1 in which the chiral organic nitrogenous base is an α-monosubstituted alkylamine.

6. A process according to claim 5 in which the α-monosubstituted alkylamine is an α-monosubstituted ethylamine.

7. A process according to claim 6 in which the α-monosubstituted ethylamine is an α-phenylethylamine in which the phenyl ring may be substituted by one or more $C_{1-4}$ alkyl, $C_{1-4}$ alkoxy or halogen groups.

8. A process according to claim 7 in which the enantiomer of the α-phenylethylamine is selected from (−)-α-methylbenzylamine, (−)-α-(2-methoxyphenyl)ethylamine, (−)-α-4-isopropylphenyl)ethylamine, (−)-α-3-(chlorophenyl)ethylamine, (−)-α-(4-fluorophenyl)ethylamine, (−)-α-(3-fluorophenyl)ethylamine, (−)-α-(2-fluorophenyl)ethylamine and (−)-α-(2-chlorophenyl)ethylamine.

9. A process according to claim 1 in which the mixture is heated at a temperature of 90°–150° C.

10. A process according to claim 9 in which the temperature is 95°–130° C.

11. A process according to claim 1 in which the mixture is heated for 8–96 hours.

12. A process according to claim 1 in which the ratio of the salt to the diluent is from 1:1 to 1:100 w/v.

13. A process according to claim 12 in which the ratio is from 1:5 to 1:15 w/v.

14. A process according to claim 1 in which the solubility of the salt of the racemic acid is from 0.5 to 2% w/v.

15. A process according to claim 1 in which 50 to 98% by weight of the salt is undissolved in the diluent at the operating temperature.

16. A process according to claim 15 in which 80 to 95% by weight of the salt is undissolved.

17. A process according to claim 1 in which the diluent is a liquid at the temperature at which the mixture is heated and is of low polarity.

18. A process according to claim 17 in which the diluent is a mixture of hydrocarbons which are predominantly aliphatic and has a boiling point in the range 110°–135° C.

19. A process according to claim 1 in which the diluent is a liquid at the temperature at which the mixture is heated and comprises a nonpolar diluent.

20. A process according to any one of claims 1 or 5 through 19, wherein the 2-arylpropionic acid is 2-(2-fluoro-4-biphenylyl)propionic acid.

21. A process according to any one of claims 2, 3 or 4 in which the chiral organic nitrogenous base is an α-monosubstituted alkylamine.

22. A process according to any one of claims 2, 3 or 4 in which the chiral organic nitrogenous base is an α-monosubstituted ethylamine.

* * * * *